(12) United States Patent
Pretorius et al.

(10) Patent No.: US 9,198,634 B2
(45) Date of Patent: Dec. 1, 2015

(54) MEDICAL DECISION SUPPORT SYSTEM

(75) Inventors: Eugene Pretorius, Western Cape Province (ZA); Otto Marsél Strydom, Western Cape Province (ZA); Matthys Louwrens Cronje, Western Cape Province (ZA); Willem Lodewyk Schoonbee, Capri Village (ZA); Michiel Mayne Blanckenberg, Western Cape Province (ZA)

(73) Assignee: DIACOUSTIC MEDICAL DEVICES (PTY) LTD, Stellenbosch (ZA)

( * ) Notice: Subject to any disclaimer, the term of this patent is extended or adjusted under 35 U.S.C. 154(b) by 354 days.

(21) Appl. No.: 13/388,617

(22) PCT Filed: Aug. 3, 2010

(86) PCT No.: PCT/IB2010/001923
§ 371 (c)(1),
(2), (4) Date: Feb. 2, 2012

(87) PCT Pub. No.: WO2011/015935
PCT Pub. Date: Feb. 10, 2011

(65) Prior Publication Data
US 2012/0130263 A1    May 24, 2012

(30) Foreign Application Priority Data
Aug. 3, 2009    (ZA) ................................ 2009/05310

(51) Int. Cl.
*A61B 5/0472*    (2006.01)
*A61B 7/04*    (2006.01)
(Continued)

(52) U.S. Cl.
CPC .................. *A61B 7/04* (2013.01); *A61B 5/0245* (2013.01); *A61B 5/0452* (2013.01); *A61B 5/0472* (2013.01); *A61B 5/7239* (2013.01)

(58) Field of Classification Search
CPC .................................. A61B 7/04; A61B 7/045

USPC .................................................. 600/528, 509
See application file for complete search history.

(56) References Cited

U.S. PATENT DOCUMENTS 7,130,429 B1    10/2006  Dalgaard
2005/0149136 A1    7/2005  Siejko et al.
(Continued)

FOREIGN PATENT DOCUMENTS

WO    WO2008/000255    1/2008
WO    WO2010/076740    7/2010

OTHER PUBLICATIONS

A.A. Sepehri et al. "A Novel Method for Pediatric Heart Sound Segmentation Without Using the ECG", Elsevier, Computer Methods and Programs in Biomedicine vol. 99, Jul. 2010, (pp. 43-45, section 4.3).
(Continued)

*Primary Examiner* — Alyssa M Alter
(74) *Attorney, Agent, or Firm* — Hamre, Schumann, Mueller & Larson, P.C.

(57) ABSTRACT

A process for pre-processing recorded and digitized heart sounds and corresponding digitized ECG signals is provided. The pre-processed signals (203) are suitable for input into an automatic decision support system implemented by means of a diagnostic decision network (205), used for diagnosing and differentiation between normal/functional (206) and pathological (207) heart murmurs, particularly in pediatric patients. The process includes identifying or predicting locations of individual heart beats within the heart sound signal, identifying the positions of the S1 and S2 heart pulses within the respective heart beats, predicting and identifying the locations and durations of the systole and diastole segments of the heart beats (302), determining if segmentation of the heart sound signal is possible based on the selected and isolated heart beats (305), and the segmentation of the respective heart beats into segments for allowing better feature extraction. The invention also provides a process for detecting the QRS complex of an ECG signal for optimizing the number of heart beat cycles detected.

12 Claims, 12 Drawing Sheets

(51) Int. Cl.
*A61B 5/0245* (2006.01)
*A61B 5/0452* (2006.01)
*A61B 5/00* (2006.01)

(56) References Cited

U.S. PATENT DOCUMENTS

2005/0222515 A1  10/2005  Polyshchuk et al.
2008/0077029 A1  3/2008  Mohler et al.
2009/0192401 A1  7/2009  Ravindran

OTHER PUBLICATIONS

Sepehri, A.A. et al. A novel method for pediatric heart sound segmentation without using the ECG, Computer Methods and Programs in Biomedicine, vol. 99, Jul. 2010, pp. 43-48, Section 4.3.

MEDICAL DECISION SUPPORT SYSTEM

FIELD OF THE INVENTION

The present invention relates to a medical decision support system for use in the diagnosis of heart murmurs in patients. More particularly, the invention relates to the pre-processing of recorded digital heart signals and sounds for use in a medical decision support system, to make the signals more useful in diagnosis and differentiation between functional and pathological heart murmurs, particularly in paediatric patients.

BACKGROUND TO THE INVENTION

Cardiac auscultation refers to the process of determining cardiac well-being or illness by listening to the heart through a stethoscope. The results obtained by means of these techniques can, however, be very subjective and depend to a large extent on the experience and acquired knowledge of the diagnosing health care worker.

The majority of cardiac abnormalities manifest themselves as cardiac murmurs. However, not all murmurs are pathological. Innocent heart murmurs are sounds made by blood circulating through heart chambers and valves or blood vessels near the heart. Innocent heart murmurs are more common in children and are considered to be harmless.

Echo-cardiography is a technique which is considered by many to be one of the, if not the, most accurate aids in the field. It utilises ultrasound technology to generate visual images of the beating heart, but requires advanced training, skill and experience to manipulate the ultrasound probe in order to obtain useful images. An echo-cardiography system will, however, require an investment of close to ZAR1 Million at the time of writing, excluding costs associated with, for example, the training of staff to operate the system and meaningfully analyze the images obtained. This high cost means that echo-cardiography systems are not a feasible option for the majority of healthcare institutions in less affluent areas.

It is estimated that up to 90% of paediatric patients will exhibit some form of heart murmur on examination, although less than 1% will eventually turn out to have a congenital heart defect. Although most paediatric cardiologists can diagnose an innocent heart murmur with a very high degree of accuracy, sensitivity and specificity, even a routine paediatric cardiology evaluation is generally too costly for people from middle to low income groups.

This is particularly true in the context of a large number of developing countries, such as South Africa, where, in addition to the high cost of paediatric cardiology evaluations, patients often have to travel long distances from rural communities in order to visit one of the few paediatric cardiologists available for the population of approximately 48 million people. The referral of paediatric patients to paediatric cardiologists can therefore become extremely difficult and in most cases impractical from a logistical point of view.

When a serious congenital cardiac defect goes undetected, the physical, socio-economical and emotional damage to the patient and his or her caretakers can be enormous.

It is therefore of the utmost importance that private healthcare physicians and nurses who look after paediatric patients must be able to determine which patients will require additional evaluation as well as the urgency with which such evaluation should be conducted.

The only assistance presently available to healthcare workers to evaluate heart sounds is the common stethoscope, which can be either mechanical or electronic. Besides the rate and frequency (pitch) of the heart sounds, morphological features, which might provide an important indication of a critical heart disorder, may be undetectable by the human ear.

A low cost, portable, digital system for analyzing heart sounds and making preliminary diagnoses would therefore be a very useful instrument to healthcare workers operating in the field. In order to be useful in such an automated system, recorded heart sounds must, however, be digitised and pre-processed for optimal feature extraction. Only once such pre-processing has been done will the signals be useful in a decision making network. Naturally, the more accurately features can be extracted, the more accurate the resulting diagnoses may be.

In the remainder of this specification the term "QRS complex" should be understood as a name for some of the deflections seen on a typical electrocardiogram (ECG) signal. It is usually the central and most visually obvious part of the tracing. It corresponds to the depolarization of the right and left ventricles. Classically the ECG tracing has 5 deflections, arbitrarily named P to T waves (in some conditions there is a U wave as well). The Q, R and S waves occur in rapid succession, do not all appear in all leads and reflect a single event so are thus normally considered as a whole complex. A Q-wave is any downward deflection after the P-wave. An R-wave is an upward deflection and the S wave is any downward deflection after the R-wave. In the remainder of this specification the term "QRS peaks(s)" should be interpreted as having a corresponding meaning.

OBJECT OF THE INVENTION

It is accordingly an object of this invention to provide a process for pre-processing recorded heart sound signals to render them useful in an automated digital decision support system, which will at least partially alleviate the abovementioned problems.

SUMMARY OF THE INVENTION

In accordance with this invention there is provided a process for pre-processing a digitised acoustic heart sound signal of a patient comprising the steps of identifying or predicting locations of individual heart beats within the heart sound signal, predicting locations and durations for systole and diastole segments of the heart sound signal, compiling a peak array containing peak locations within the heart sound signal that correspond to possible locations of S1 and S2 heart sound pulses in the heart sound signal, calculating interval sizes between the peak locations in the peak array, selecting and isolating heart beats in the heart sound signal that were detected with the highest level of confidence based on the predicted durations of the systole and diastole segments of the heart sound signal and the peak array, determining if segmentation of the heart sound signal is possible based on the selected and isolated heart beats, dividing inter-peak intervals that make up the heart sound signal into even and odd groups in the order in which they appear if segmentation of the heart sound signal was found to be possible, and calculating the variance and mean for both groups and taking the group with the largest ratio of variance over mean as corresponding to the diastole intervals and the other group as corresponding to the systole intervals.

Further features of the invention provide for the step of predicting the durations of the systole and diastole segments of the heart sound signal to further comprise the steps of calculating an envelope signal from the heart sound signal, applying a peak-peeling algorithm to the envelope signal of the heart sound signal to create a peaks signal, finding the peak locations within the heart sound signal by means of a peak finding algorithm which utilised the peaks signal, predicting an average resting heart rate for the patient based on the age of the patient, determining whether the peak finding algorithm has found peak locations corresponding to both S1 and S2 heart sounds in the heart sound signal or only one of them by calculating heart rates representative of both scenarios based on the distances between the peak locations in the peak array, and comparing the calculated heart rates to the average resting heart rate, and if it is determined that both the S1 and S2 heart sounds were found by the peak finding algorithm, predicting the duration of the systole and diastole segments of the heart sound signal by using Burke's formula for male or female patients, as the case may be.

Still further features of the invention provide for the step of calculating the envelope signal from the heart sound signal to further comprise the steps of splitting the heart sound signal into short segments and calculating a principal component for each segment, the principal components of each segment forming the envelope signal; and for the process to include the step of determining a second prediction of the durations of the systole and diastole segments of the heart sound signal by calculating an autocorrelation of the peaks signal to obtain an autocorrelation signal, locating a central peak and three other peaks closest to the central peak in the autocorrelation signal and determining the average systole and diastole durations based on the intervals between these peaks.

Yet further features of the invention provide for the process to include the step of refining the peak locations in the peak array by setting a minimum and a maximum threshold for the systole duration, marking intervals between peak locations that fall within the minimum and maximum thresholds as possible systolic intervals, identifying an interval that is shorter than the minimum threshold as an irregular interval, the irregular interval being positioned between a first and second peak location in the peak array, removing the second peak location from the peak array if an interval immediately before the irregular interval has been marked as a systolic interval, or removing a smaller of the first and second peak locations from the peak array if neither the interval immediately before the irregular interval, nor an interval immediately thereafter has been marked as a systolic interval, and repeating the steps until no peaks were added or removed during a last iteration; and for the step of setting the minimum and maximum threshold for the systole duration to include setting the minimum duration at 80% of an average systole length and setting the maximum duration at 120% of the average systole length.

Further features of the invention provide for the step of refining the peak locations in the peak array to include the step of recovering potentially lost peaks, which in turn includes the steps of setting a maximum threshold for a diastole duration, identifying an interval that is longer than the maximum threshold as an irregular interval corresponding to a potentially missing peak, the irregular interval being positioned between a first and second peak location in the peak array, assuming the missing peak to be in the irregular interval, searching for the missing peak by looking for a maximum value in a corresponding region in the envelope signal, adding a peak to the peak array at a position corresponding to the maximum value if the maximum value is higher than a fixed threshold, alternatively, looking for a second maximum value in a Shannon energy envelope of the heart sound signal and adding a peak to the peaks array if the second maximum value is above a threshold, alternatively, adding no additional peak in the peak array; and repeating the steps until no changes were made to the peaks array during a last iteration; and for the step of setting the maximum threshold for the diastole durations to include setting the maximum threshold at 120% of an average diastole length.

Still further features of the invention provide for the step of selecting and isolating the most confidently detected heart beats to further include the steps of calculating a nominal heart rate for the patient by determining the autocorrelation of the heart sound signal, calculating the instantaneous heart rate for every heart beat represented by 2 adjacent peak intervals in the peak array, comparing the instantaneous heart rate for every heart beat to the nominal heart rate, and disregarding heart beats of which the instantaneous heart rate differs from the nominal heart rate by more than a predefined percentage and regarding the others; for the predefined percentage to be 15%; and for the step of determining if segmentation of the heart sound signal is possible to include the step of determining if more than a predefined number of consecutive heart beats have been regarded.

The invention further provides a process for detecting QRS peaks in a digitised ECG signal, the process comprising the steps of filtering the digitised ECG signal, calculating the derivative of the filtered, digitised ECG signal, determining a Hilbert Envelope for the signal, determining peak locations within the signal by means of a peak peeling method, smoothing the peaks in the signal positioned in close proximity to one another by integrating the signal, determining starting positions of the QRS peaks by identifying rising edges in the signal, analysing the results obtained in the previous step for anomalies, identifying and marking anomalies and, if identified, repeating the process from where the derivative of the signal is calculated, with the areas in the signal corresponding to the anomalies removed, finding the QRS peaks within the original filtered ECG signal by utilising the starting positions of the QRS peaks if no anomalies are identified, and filtering the detected QRS peaks for irregularities by comparing durations between peaks with average peak durations and a detected variance of these durations.

The invention still further provides a method of segmenting the heart beats that make up a digitised acoustic heart sound signal comprising the steps of pre-processing the heart sound signal, in accordance with a process as described above, if the heart sound signal is capable of being segmented; or if the heart sound signal is not capable of being segmented, detecting QRS peaks in a digitised ECG signal corresponding to the heart sound signal in accordance with a process as described above, and using the QRS peaks to segment the heart sound signal.

Further features of the invention provide for the step of segmenting the heart sound signal using the QRS peaks to include the steps of detecting the S1 and S2 heart sound components by segmenting the heart sound signal into its constituent heart beats by using the ECG signal's QRS peaks, using all heart beats with a corresponding detected QRS peak to calculate an average heart beat period, band pass filtering the heart beats between 40 Hz and 80 Hz, calculating a heart beat envelope signal from the filtered signal, smoothing the envelope signal by means of an integration filter, and segmenting the S1 and S2 heart sound components, S1 corresponding to a first peak and S2 to a second peak in the smoothed envelope signal, and filtering the heart beats using the wavelet method to eliminate background noise; and for the step of segmenting the S1 and S2 heart sound components to include the steps of segmenting the S1 heart sound component from the QRS peak to where the smoothed envelope signal reaches a first minimum, and segmenting the S2 heart sound component from its start, which is found by searching in a region after the S1 heart sound component for the onset of the second peak, to its end, which corresponds to the end of the second peak.

The invention yet further provides a method of parsing a digitised acoustic heart sound signal into its constituent heart beats comprising the steps of detecting QRS peaks in a digitised ECG signal corresponding to the heart sound signal in accordance with a process as described above, and using the QRS peaks to identify the individual heart beats that make up the heart sound signal, it being assumed that each QRS peak corresponds to a different heart beat.

BRIEF DESCRIPTION OF THE DRAWINGS

The invention will now be described, by way of example only with reference to the accompanying representations in which.

DETAILED DESCRIPTION WITH REFERENCE TO THE DRAWINGS

Figure 1:
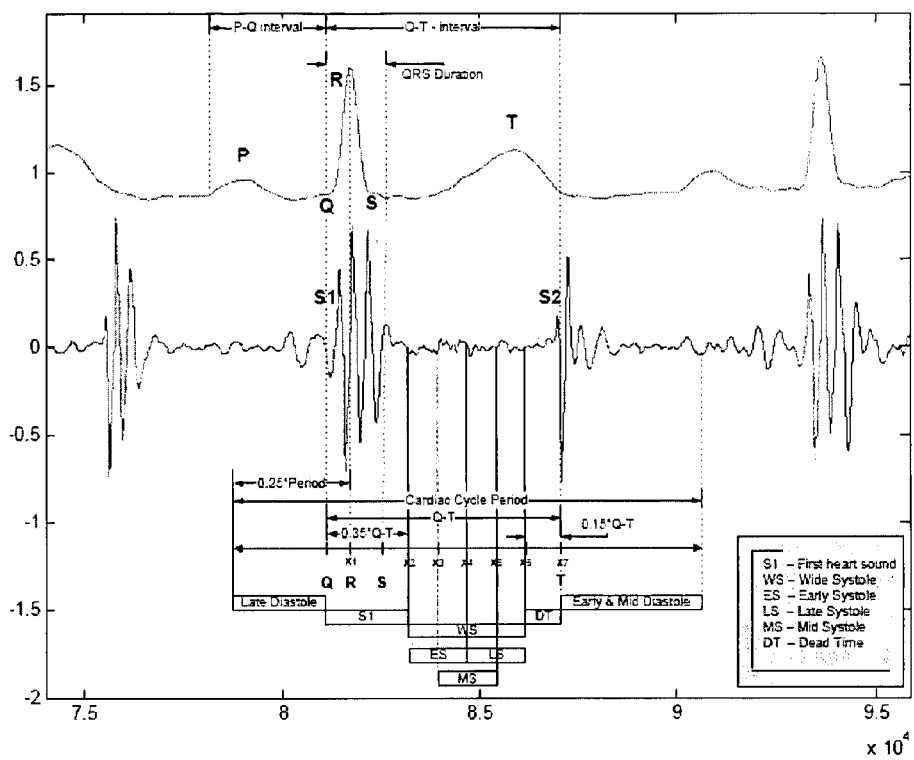
FIG. 1: is a graph showing the heart sound period cycle with its corresponding ECG signal.

In the drawings, FIG. 1 illustrates a graph showing an electrocardiogram ("ECG") signal (1) and an acoustic heart sound signal (2). In the graph, S1 represents a first heart sound, WS represents a wide systole, ES represents an early systole, MS represents a mid systole, DT represents dead time, and S2 represents a second heart sound. The letters P, Q, R, S and T represent the turning points in the electrical activities of the cardiac cycle represented by the ECG signal.

Figure 2:
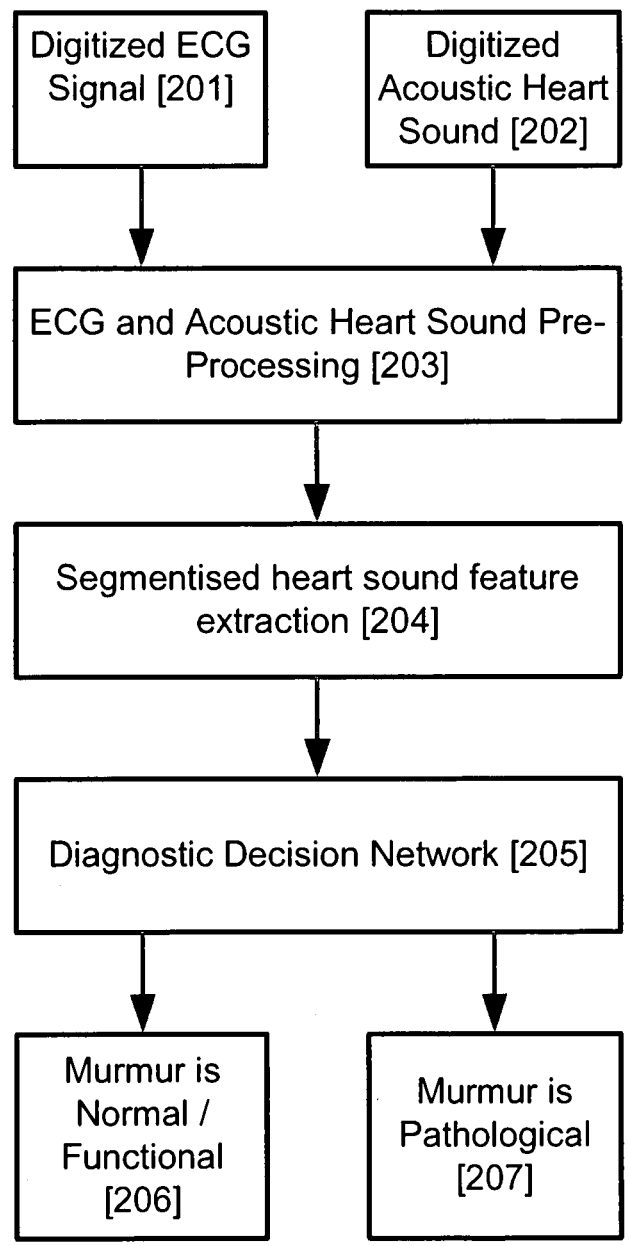
FIG. 2: is a system flow diagram indicating the inputs, pre-processing, decision network and outputs.

As shown in broad outline by the flow diagram of FIG. 2, to enable an automated system to distinguish between pathological (207) and normal or functional (206) heart murmurs, the ECG signal (201) and/or the associated acoustic heart sound signal (202) must be digitised and pre-processed (203), and segmented (204) for optimal feature extraction for input into a decision network (205).

It is with this pre-processing at step (203) that the current invention is primarily concerned.

The means for receiving the digitized acoustic heart sound at step (202) may include an electronic stethoscope placed on the chest of the patient, analogue circuitry including amplifiers, analogue filters and an analogue-to-digital converter.

Likewise, the means for receiving the digitised ECG signal at a step (201) may include three ECG leads with ECG electrodes connected to it, an analogue differential amplifier with a feedback line, analogue filters and an analogue-to-digital converter.

The pre-processing of the digitised acoustic heart sound and digitised ECG signal at step (203) includes the steps of digitally filtering the respective signals, determining the presence of an acoustic heart sound and ECG signals, locating the positions of the S1 and S2 heart sounds within the respective heart beats that make up the heart sound signal, locating the QRS peak within the respective ECG periods and parsing the recorded digitized acoustic heart sound within its respective heart beat cycles.

At step (204), the heart beat cycles are then segmented and specific features are extracted from them. The segmentation includes the division of the heart beat cycles into a predetermined number of segments and the feature extraction includes calculating the power spectrum and features of each segment as input to the diagnostic decision network shown at step (205).

The diagnostic decision network shown at step (205) is then implemented by means of a neural network which indicates that the input heart sound is either normal, at step (206), or contains a murmur associated with a predefined pathology, at step (207). It should, however, be noted that the operation of the diagnostic decision network does not form part of the current invention.

Figure 3:
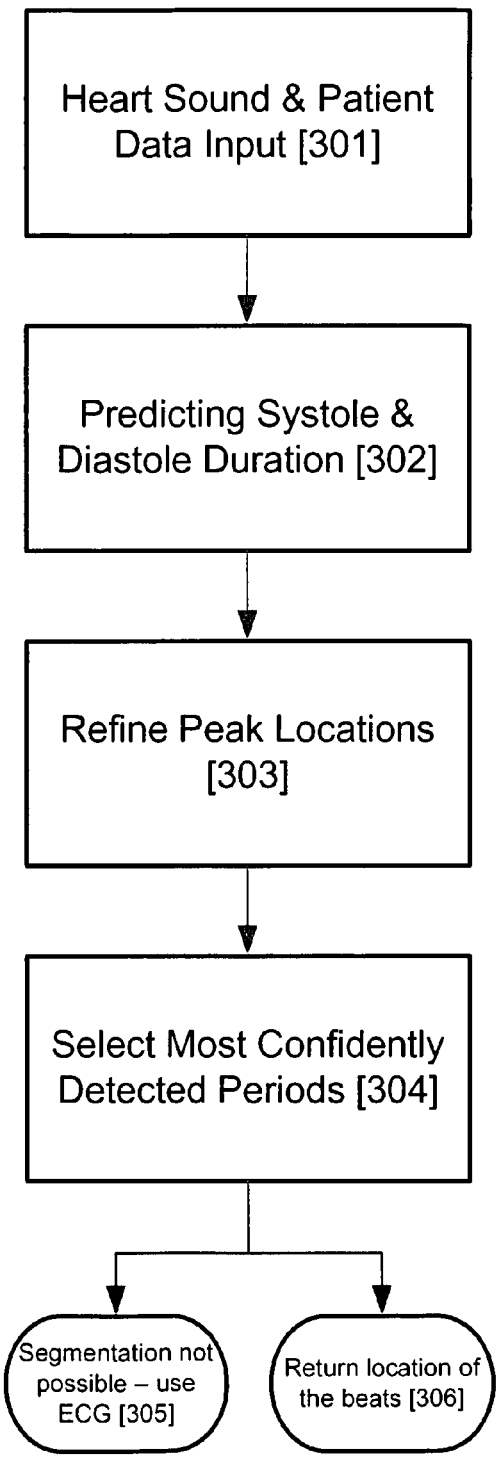
FIG. 3: is a high level flow diagram of the S1 and S2 finding algorithm.

In order to locate the S1 and S2 positions within the digitised heart sound the steps shown in the flow diagram in FIG. 3 are followed. The recorded, digitized heart sound, along with patient data such as, for example, the patient's age and sex, are used as inputs at step (301). The envelope of the heart sound signal is then determined and the duration of the systole and diastole segments of the heart sound are predicted at step (302). Next, peaks that correspond to possible S1 and S2 locations are determined at step (303). By using this knowledge (predicted systole and diastole duration and peak locations) as inputs, the periods (heart beats) detected with the highest level of confidence are selected and isolated at step (304). This information is then used to determine if segmentation of the signal is possible at step (305). Only if at least five consecutive beats could be identified in the heart sound signal, is segmentation considered to be possible. This is expanded on further below. If segmentation was not possible, the ECG signal must be used for further analysis or the recording of the heart sound signal must be repeated. Alternatively, if segmentation was found to be possible, the locations of the individual heart beats are returned at step (306).

Figure 4:
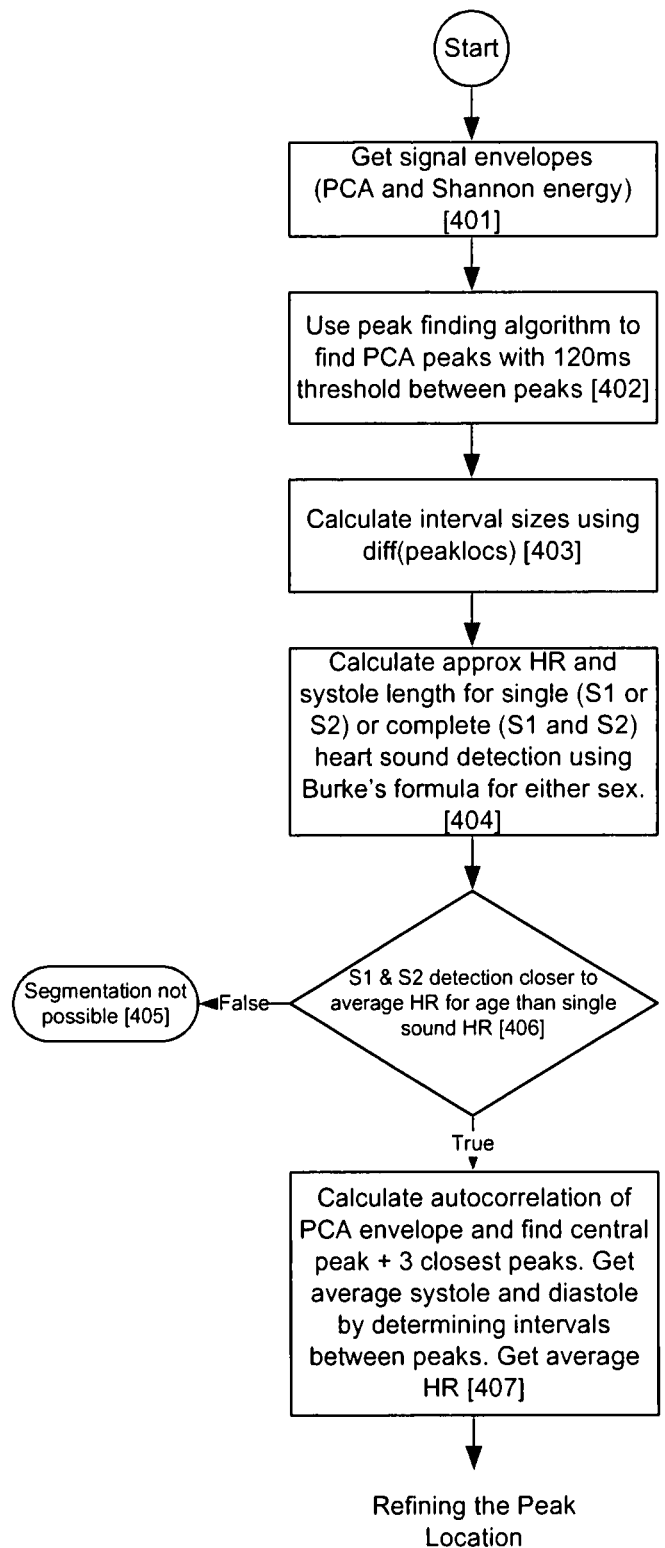
FIG. 4: is a flow diagram for determining the systole and diastole duration, the first step in determining the position of S1 and S2.
Figure 7:
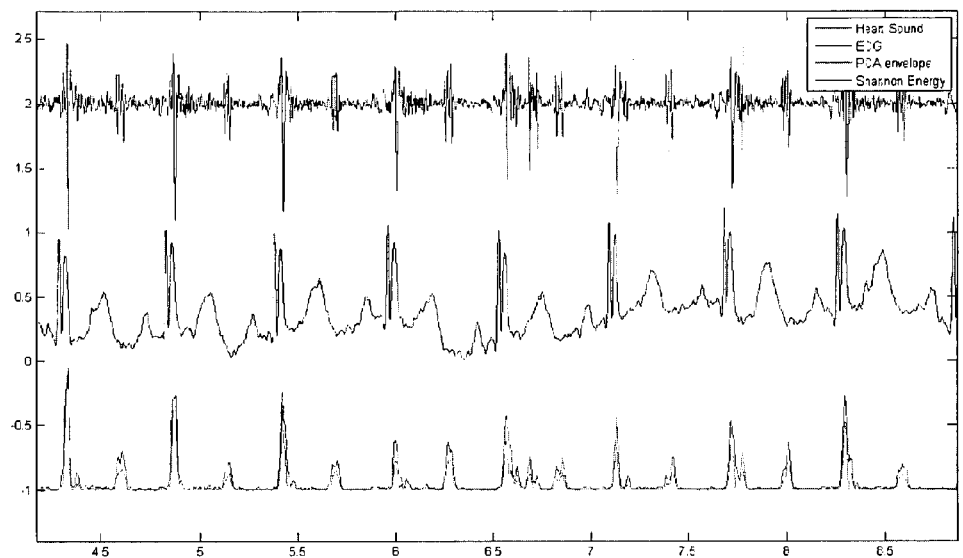
FIG. 7: shows the envelope calculation results showing the phono-cardiogram recording, the ECG recording, the PCA envelope and the Shannon Energy.

To predict the systole and diastole duration as mentioned in relation to step (302) above, the flow diagram shown in detail in FIG. 4 is utilised. The first step at (401) is to calculate an envelope of the signal from which peaks can be extracted. An envelope of the heart sound can be constructed by splitting the heart sound into short segments and calculating a Principal Component for each segment. The Principal Components (PCs) of each segment then form a new signal (the envelope). The peaks in such an envelope correlate very well with low entropy sounds like S1 and S2. Murmurs usually have higher entropy (more randomness) and therefore the PCs of these sounds are not as distinct. See FIG. 7 for an example of an envelope signal.

Principal Components Analysis (PCA) is a useful method of identifying patterns in data. It is often used to reduce data dimensionality by highlighting differences and similarities between different data sets.

A peak-peeling algorithm is then applied to the PCA envelope of the heart signal at step (402). This algorithm iteratively adds the part of the signal above the standard deviation of the signal to a new 'peaks' signal whilst subtracting (removing) the added peaks from the original signal to find the signal from which the next round of peaks will be peeled. This procedure is repeated until the standard error between iterations of pealing is sufficiently small. This threshold can be adjusted to determine how 'deep' the peak peeling algorithm goes to find peaks.

Figure 8:
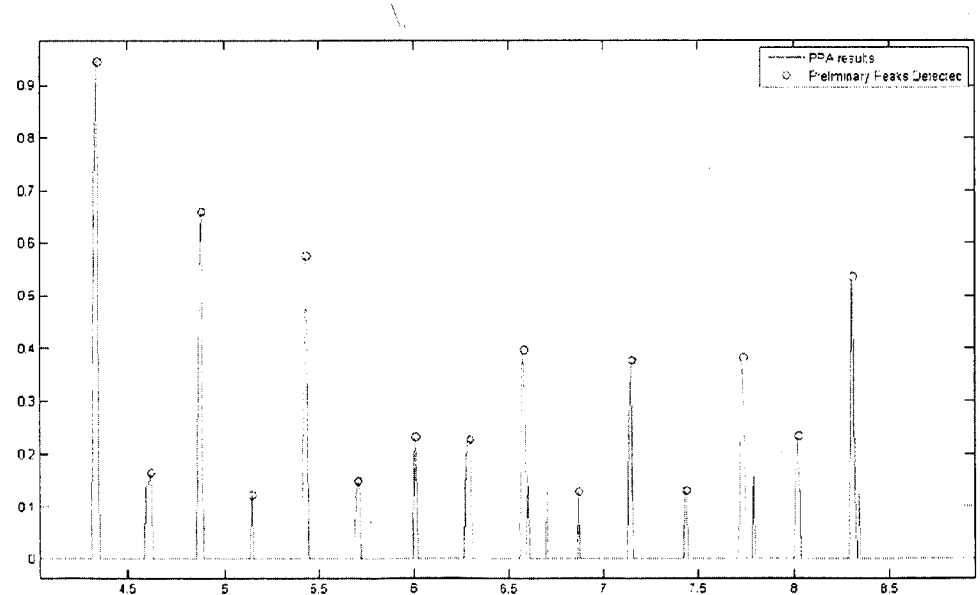
FIG. 8: shows the results of the peak-peeling algorithm and preliminary peaks.

The peaks envelope (peaks signal) that is returned is then passed to a peak finding algorithm that finds the locations of the peak positions in the heart sound signal. This algorithm only returns the largest local maxima separated by a buffer of a few milliseconds. The buffer value is set to the average distance for the detected S1 and S2 durations. By doing this, extra peaks, especially in the systolic region, are ignored. See FIG. 8 for results of the peak-peeling algorithm.

It is not always known at this stage whether the peak finding algorithm has in fact detected both the S1 and S2 heart sounds. In some cases either only S1 sounds or only S2 sounds may have been found. This could be as a result of the recording position used, or when, for example, a large murmur masks the S2 sound.

The patient's age is used to predict the average resting heart rate for a person of that age. Heart rates for both possible scenarios (where both heart sounds are present and where there is only one) are calculated by taking the median interval between peaks and the median interval between each second peak. These are then converted to heart rates and compared to the expected average heart rate of the patient at step (403). Depending on which is closer, it is decided at step (406) whether both sounds have been found or not. If both sounds are not detected, segmentation is not attempted without the ECG at step (405).

With an approximation for the heart rate available, Burke's formulas can be used to find the average systole and diastole durations at step (404). Different formulas for male and female patients are used and therefore the sex also has to be extracted from the database. The formulas are:

$$systole=0.3308x^3-1.084\mu x^2+1.1658x-0.0681$$

for male patients and;

$$systole=0.7678x^3-1.1991x^2+1.7956x-0.197$$

for female patients, where x is the average heart beat period (Heart Rate/60).

Figure 9:
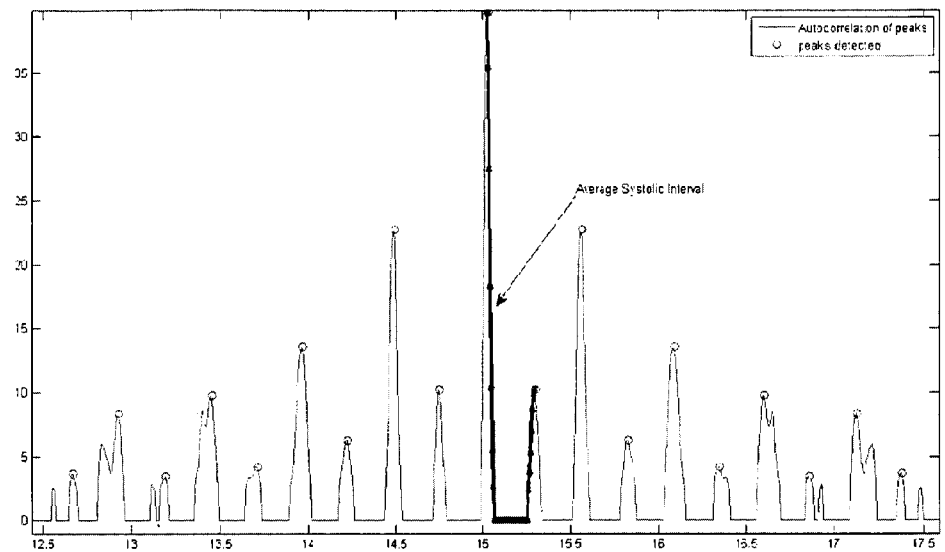
FIG. 9: shows the auto-correlation of peaks signal.

The autocorrelation of the peaks signal (PCA envelope) provides a second, more accurate, estimation for the average systole and diastole intervals at step (407). Periodicity of the signal is highlighted by peaks in the autocorrelation. In the absence of peaks caused by murmurs or a wildly varying heart rate in the recording, the time intervals to the first and second peaks after the central peak give the average systole and diastole durations. The first approximation method is necessary in order to validate these averages and serves as input for refining the peak locations. The results of this method are shown in FIG. 9.

Figure 5:
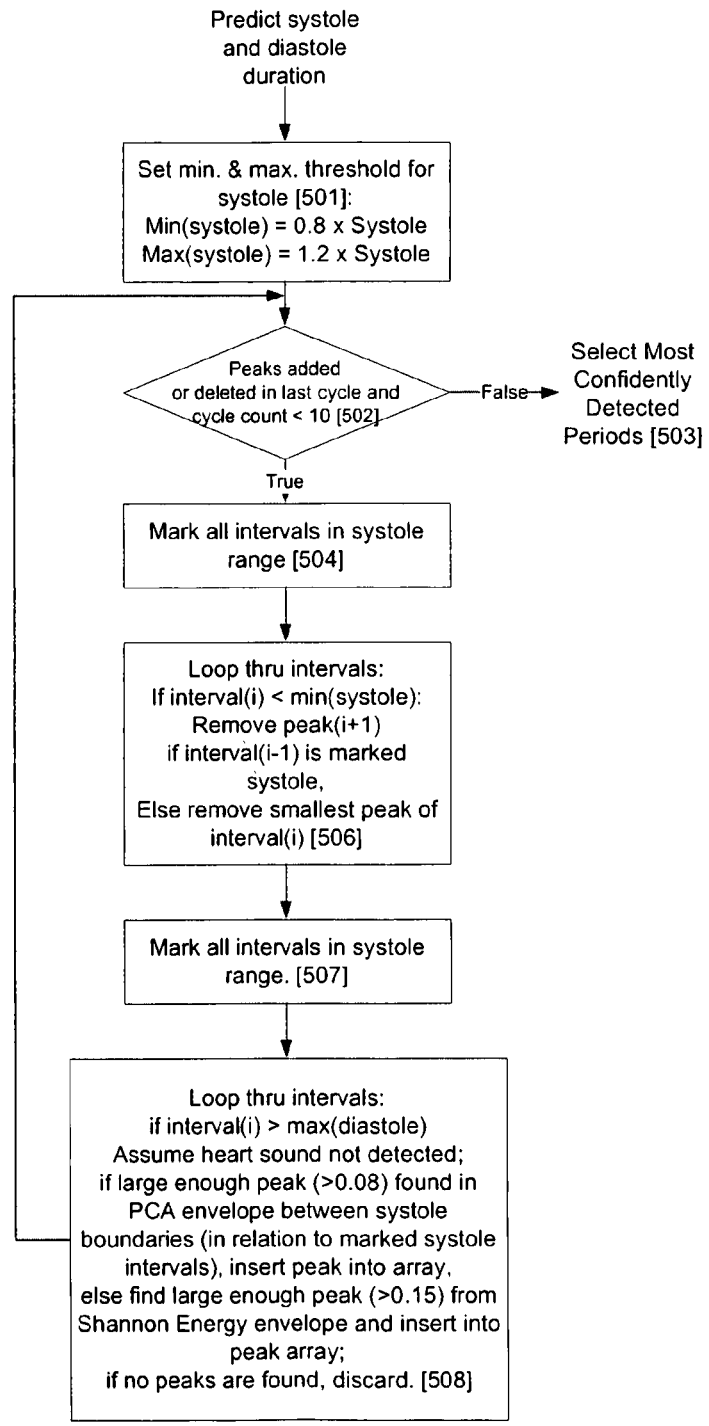
FIG. 5: is a flow diagram for refining the peak location in the PCA envelope.

The process utilised to refine the peak locations is shown in the flow diagram of FIG. 5. The systole and diastole durations predicted earlier as described above are used as inputs to this process.

In some cases extra peaks, which can generally be attributed to external noises or murmurs, are detected. An iterative algorithm was therefore developed to remove these peaks from the array of peak indices at step (502). A minimum duration for the systolic interval of 80% and a maximum of 120% of the average systole length is calculated at step (501). All intervals between peaks that fall in this range are then marked as possible systolic intervals at step (504).

When an interval shorter than the minimum systole length is found, it is assumed to be a false peak. When this occurs and the previous interval was marked as a systole at a step (507), the second peak is deleted in order to keep the integrity of systole lengths. When neither the previous interval nor the next interval is marked as a systole, the smaller of the two peaks marking the interval is deleted at step (506).

In order to recover lost peaks, a maximum diastole length of 120% of the average diastole length is calculated. Wherever an interval is found to be longer than this maximum, it is assumed that a peak is missing. The peak is assumed to be in the region between the minimum systole lengths from the adjacent peaks. The maximum value of the PCA envelope in this region is returned. If this value is not higher than a fixed threshold, the Shannon energy envelope is used. If that value is above a threshold, the peak is added to the peaks array, if not, it is discarded at step (508).

Figure 10:
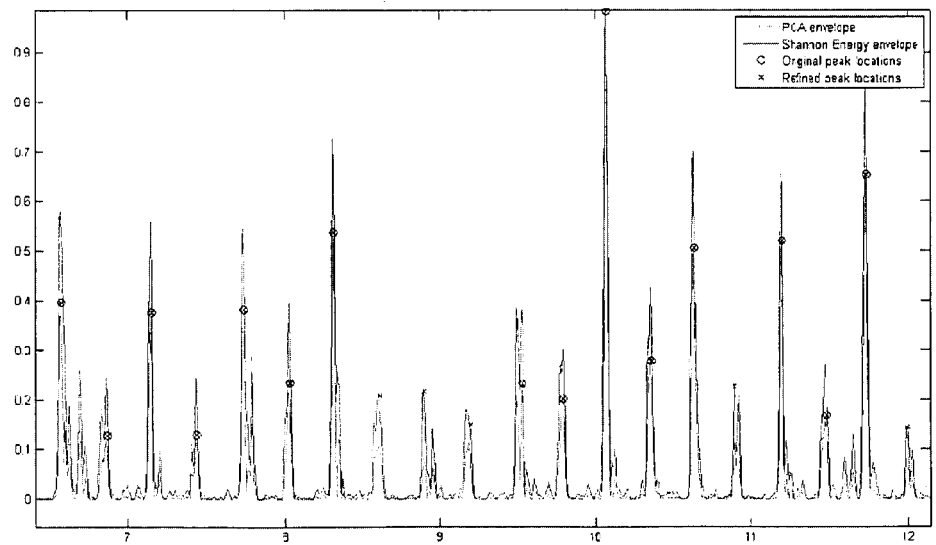
FIG. 10: shows the peak detection refinement.

The process of rejecting false peaks and recovering missing peaks is repeated until no changes were been made to the peaks array during the last iteration. The results of this process are shown in FIG. 10.

Figure 6:
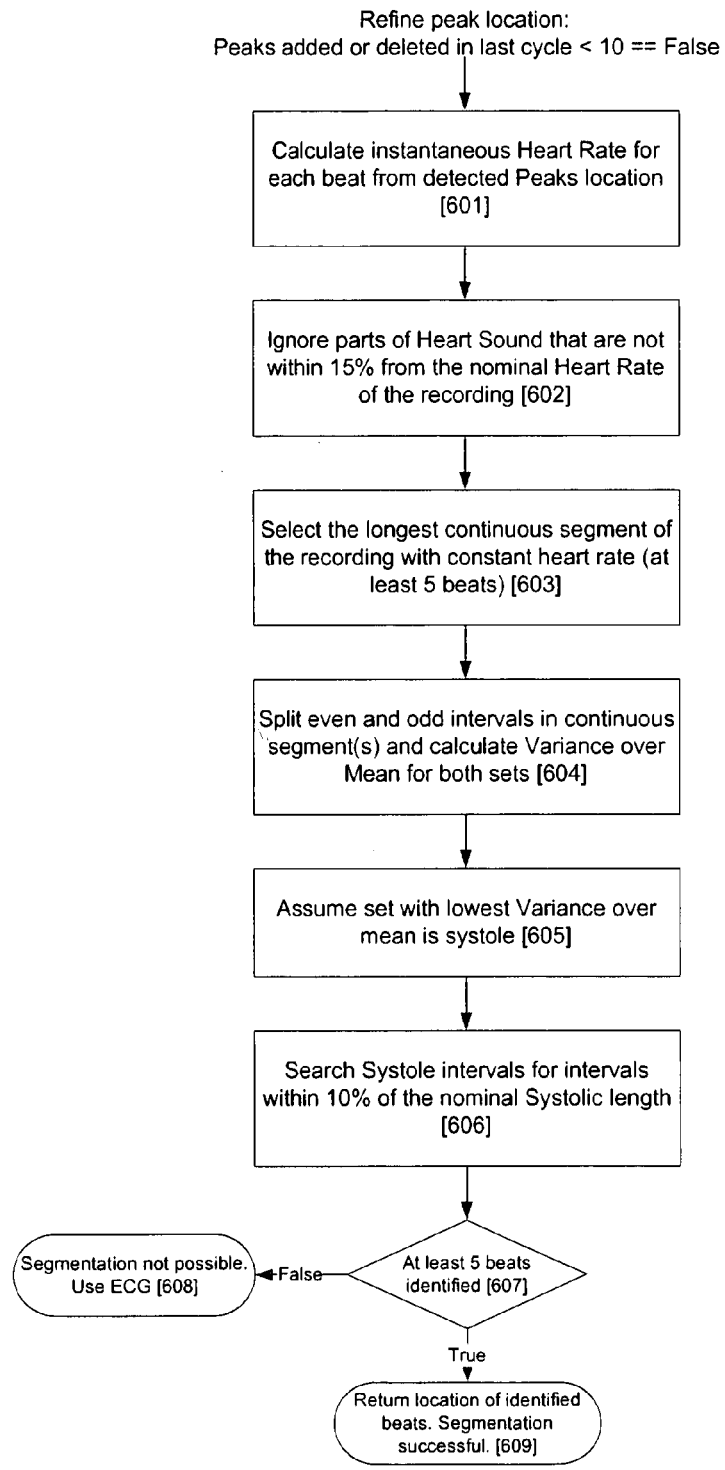
FIG. 6: is a flow diagram for selecting the most confidently detected peaks.

The flow diagram shown in FIG. 6 represents the process that is followed for selecting the most confidently detected S1 and S2 peaks (heart beats), the output of the process as described above with reference to FIG. 5 is used as input to this process. The instantaneous heart rate for every heart beat (2 adjacent peak intervals) in the peak array is firstly calculated at a step (601). Where the instantaneous heart rate differs by more than 15% from the nominal heart rate of the recording, as determined by autocorrelation, that beat is not considered for further use at a step (602). This process removes beats with a large likelihood of missing a peak or having an extra peak. Poor recordings and severe arrhythmias are also thereby rejected.

The remaining beats that fall within the required range of heart rate are used for further processing. Only where five or more consecutive beats are all in the correct range, is segmentation attempted at step (603).

The inter-peak intervals that make up these beats are then split into even and odd groups, in order at step (604). This is done to separate the systole and the diastole intervals.

The diastole duration is likely to show more variation during a recording, as it can be influenced by breathing. For each group its variance over its mean is then calculated and the one with the largest value is taken as being the diastole intervals at steps (605) and (606).

Not all the heart beats in the recording are needed to make a diagnosis, so only those most likely to be detected correctly are returned. The beats to be returned for diagnosis at step (605) are selected by selecting the systole intervals closest to the predicted average systole length. If more than five beats are returned at step (607), the recording is considered to have been segmented successfully at step (609). If not, the ECG recording must also be used as input to do segmentation at step (608).

Figure 11:
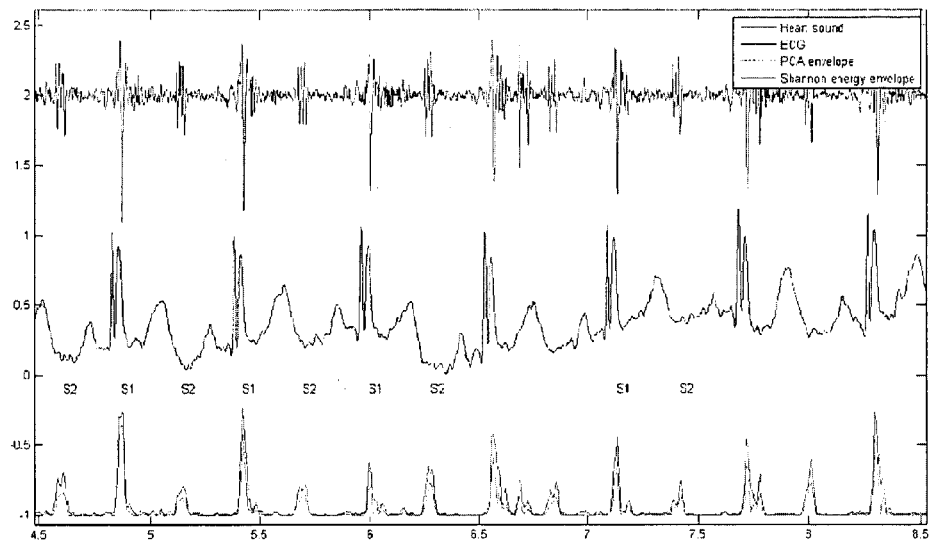
FIG. 11: shows the identified heart beats.

From these intervals the likely locations of the S1 and S2 sounds should be known, as every systolic interval starts with an S1 peak and ends with an S2 peak. The results are shown in FIG. 11.

Figure 12:
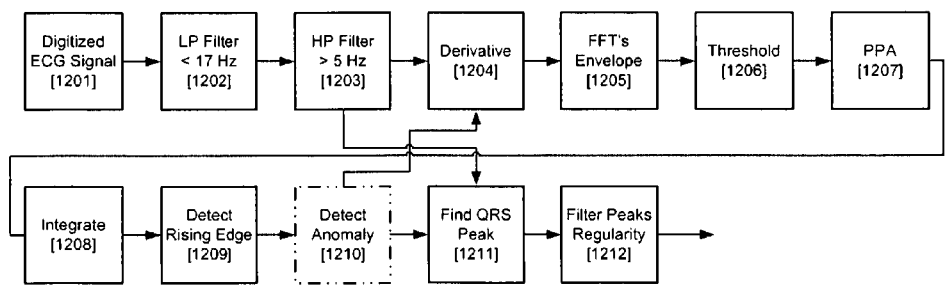
FIG. 12: shows a flow diagram of the ECG detection algorithm.

Determining the ECG QRS Peaks:

The process represented by the diagram shown in FIG. 12, describes the steps utilised for detecting the QRS peaks within the digitized ECG signal starting at step (1201). The positions of these peaks may be used as input for dividing the digitized heart sound signal into the respective heart beat periods, as well as for segmenting the detected heartbeat periods. This is, however, only done if the heart sound signal cannot be segmented as described above.

The digitized ECG signal is band passed filtered by means of a low pass filter with −3 db point at 17 Hz at step (1202) and a high pass filter with −3 db point at 5 Hz at step (1203). To calculate the slope of the filtered ECG signal, each sample is subtracted from a sample four places removed from it at step (1204). This subtraction can be indicated by the formula (x(n)−x(n−4)). The envelope of this signal is then determined by means of the Hilbert envelope method at a step (1205). Step (1205) could, for example, also utilise the Sarkady method by taking the FFT of the signal, disregarding the second or upper part of the FFT and doing an inverse FFT.

The possible peak locations are then determined at step (1207) by the same peak-peel method (PPA) as discussed with reference to step (402) above. The PPA iteratively "peels" the estimated ECG signal, gradually gathering those parts that construct its peaks. In this way, even small amplitude peaks are accurately identified to determine the most likely QRS peaks.

Peaks that would otherwise be detected relatively close to one another are then "smoothed" by integrating the signal at a step (1208). In this way the possible multiple detection of a single QRS peak is eliminated. The next step is to determine the start positions of all the possible QRS peaks by detecting an increase in the signal value from zero to a value larger than zero, a rising edge, and vice versa, a falling edge, for the end positions at step (1209). If an anomaly is detected at step (1210), the previous action is disregarded and the process is started again from step (1204). If no anomaly is detected the location of the QRS peak is determined within the original filtered signal which is present at step (1203).

The highest turning point of the signal is then determined in each of the start and end positions and used as the QRS peak at step (1211). These peaks are filtered for irregularities by comparing the duration between peaks with the average peaks durations and the detected variance of these durations at step (1212).

Figure 13:
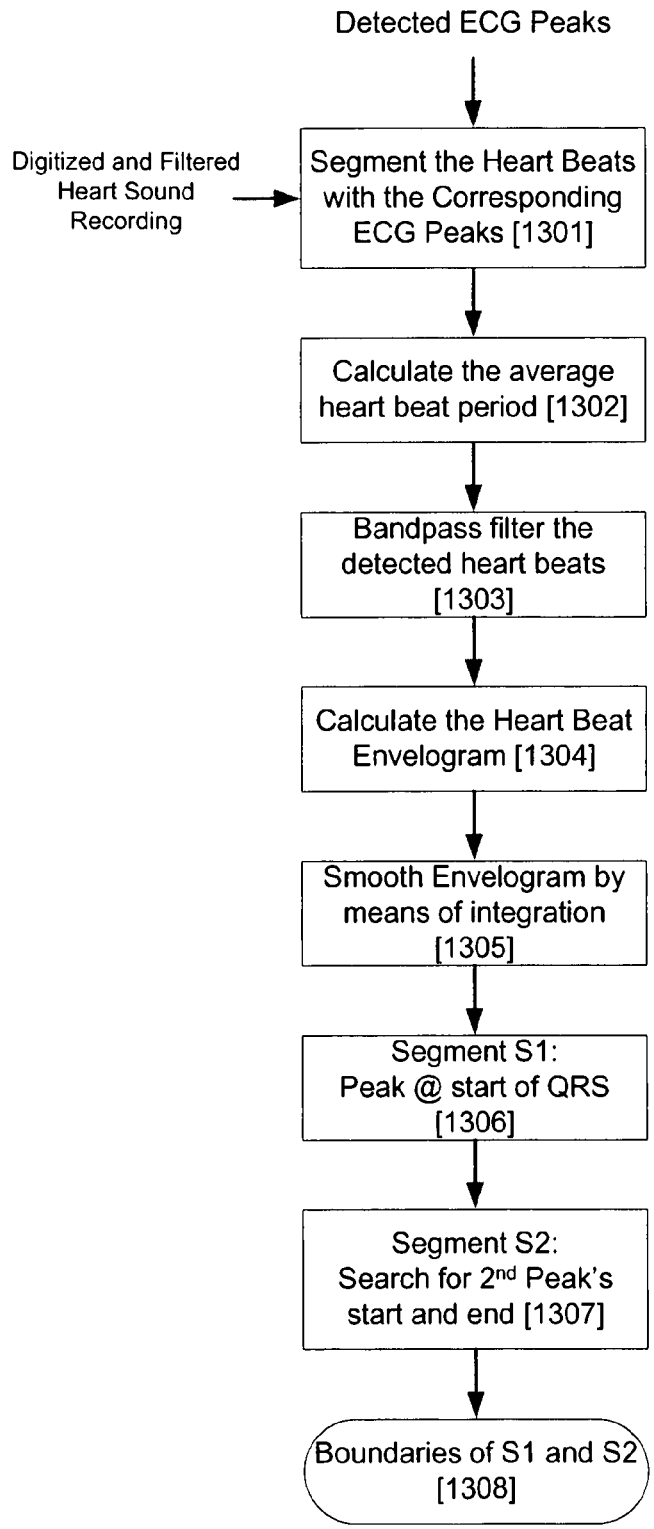
FIG. 13: shows a flow diagram of the process of detecting S1 and S2 by using the detected QRS peaks from the ECG signal as input.

Detection of S1, and consequently S2, is done using the following process described with reference to the flow diagram illustrated in FIG. 13. At a step (1301), the heart beats making up the heart sound signal are segmented using the corresponding ECG peaks determined as described above. All beats with a corresponding detected QRS peak (the output at step (1212) above), after filtering, are then used to calculate an average heart beat period at step (1302). The detected beats are then band pass filtered between 40 Hz and 80 Hz at a step (1303). A heart beat envelope (envelogram) is then calculated from the resulting signal at step (1304). The envelope is smoothed using an integration filter at step (1305) before segmenting the S1 and S2 heart sound components at steps (1306) and (1307), respectively. Ideally the envelope should contain two peaks, the first corresponding to S1 and the second to S2. S1 is segmented from the start of the QRS peak to where the envelope reaches its first minimum at step (1306). The start of S2 is found by searching in a region after S1 for the onset of the second peak and the end of S2 is found by searching for the end of the second peak at step (1307). Using this method each beat is segmented and accurate approximate boundaries for regions S1s, systoles, S2s and diastoles are found at step (1308).

The identified heart beats are filtered using the wavelet method to eliminate possible background noise. A Daubechies 2 wavelet is calculated up to level 2. The detail coefficient is used as an approximation for the signal noise. An error measure is calculated from the sum of the wavelet detailed coefficients at level 2. All beats in a signal are then arranged in order of this error measurement.

Figure 15:
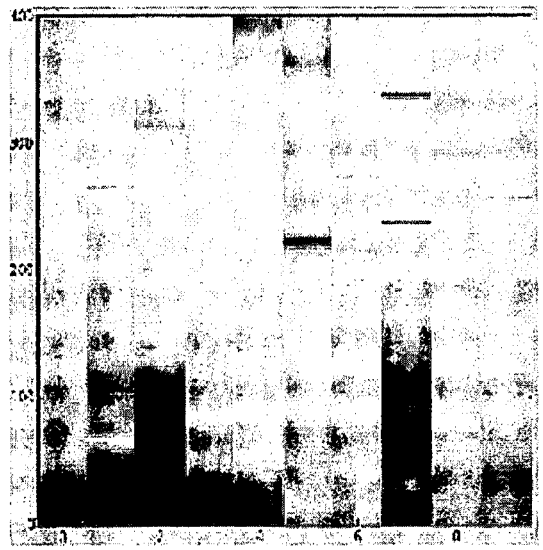
FIG. 15: shows a heart sound segmented into 10 equal bins.

With the positions of S1 and S2 known for the identified heart beats, the heart beats can be more accurately segmented, so that S1 and S2 fall into specific bins as shown in more detail in FIG. 15. This is only an example of a possible segmentation strategy with the exact position knowledge of S1 and S2.

After segmenting all the extracted heart beats into bins, the beats are normalized and the features extracted. These features can then be used as inputs to a neural network that will decide if the heart sound has a pathological murmur or not.

Figure 16:
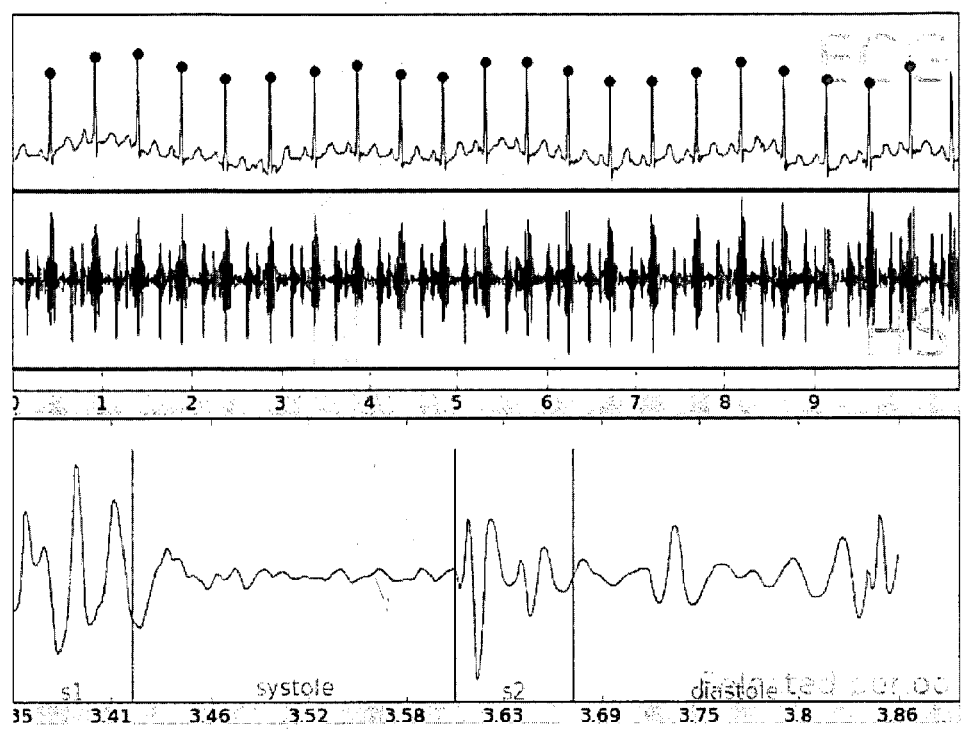
FIG. 16: shows typical results when segmenting the heart sound using the ECG signal and the recorded heart sound.

It should be appreciated that this invention deals with the parsing of a digitized and filtered heart sound signal into respective heart beats by using the electrocardiogram (ECG) signal or only the heart sound signal and identifying the S1 and S2 sound pulses as well as the systole and diastole periods within the heart sound by only using either of the two signals (the results of which is shown more clearly in FIG. 16).

Figure 14:
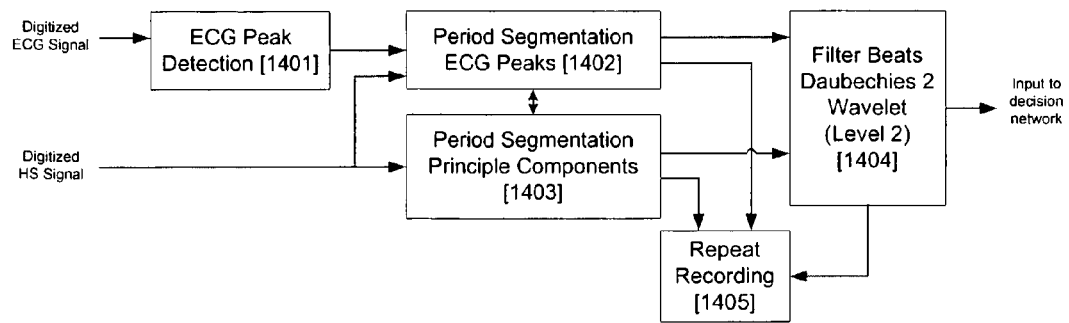
FIG. 14: is a high level flow diagram for pre-processing the ECG signal and heart sounds to segment the heart sound into heart beat periods.

The high level flow diagram shown in FIG. 14 shows the pre-processing of the ECG and heart sound signal in order to segment the heart sound signal into individual heart beats as described above.

Segmentation of the recorded heart sound is the first, and arguably the most important step in the automatic diagnosis of heart sounds. This involves separating the heart sound recording into periods that correspond to single beats. Precise knowledge of the timing of certain heart sounds are required in order to make a successful diagnosis. These heart sounds include the primary heart sounds, S1 and S2—respectively the "lub" and the "dub" characteristics of a single "lub-dub" heart beat. Heart murmurs, which could be either functional or pathological may or may not be present in the recording.

Traditionally, heart sound segmentation is done by using a simultaneous ECG recording to separate the heart beats by means of the detection of the QRS complex. This method is very accurate, especially for detecting the first heart sound (S1), which immediately follows the QRS complex. Detecting S2, the second heart sound, is then done by either detecting the T-wave in the ECG, recording the carotid pulse signal and finding the notch, or by using a formula that predicts its location using the heart rate. These additional methods are, however, very complex and not always reliable.

Detecting the QRS complex can also be a complex task, particularly on paediatric patients, due to the small electrical signals, impedance and signal variations resulting from the patient moving or the non-optimal placement of the ECG electrodes. The invention provides a novel procedure for detecting the QRS complex of an ECG signal for optimizing the number of heart beat cycles detected.

Recording the ECG signal requires the attachment of at least 3 leads to the patient which could be cumbersome and not a very practical method for scanning patients in places such as rural health clinics, where doctors and nurses are very much pressed for time. A method based on principle component analysis for calculating an envelope signal from the phono-cardiogram is also presented here. Peaks in this envelope are detected and are presumed to correlate with the S1 and S2 sounds. Post-processing based on the locations of these peaks is then done in order to classify each peak as either an S1 or S2 or an artefact that should be ignored.

The uniqueness of this invention lies in the combination of techniques used to segment the phono-cardiogram into individual heart beat cycles by using either the novel ECG peak detection process or the principle component method for detecting S1 and S2. The unique combination of these two methods could also be used to segment the heart beat cycle into a number of windows.

The above description describes the invention by way of example only and it should be appreciated that numerous modifications may be made to the embodiments described without departing from the scope of the invention.

The invention claimed is:

1. A computer-implemented process of pre-processing a heart sound signal of a patient's heart, the process being performed by a computing device and including:
    a) receiving, by the computing device, at least one recorded heart sound signal of a patient's heart in the form of a digitized acoustic heart sound signal;
    b) identifying or predicting, by the computing device, locations of individual heart beats within the digitized acoustic heart sound signal;
    c) predicting, by the computing device, locations and durations for systole and diastole segments of the digitized acoustic heart sound signal;
    d) compiling, by the computing device, a peak array containing peak locations within the digitized acoustic heart sound signal that correspond to possible locations of S1 and S2 heart sound pulses in the digitized acoustic heart sound signal;
    e) calculating, by the computing device, interval sizes between the peak locations in the peak array;
    f) selecting and isolating, by the computing device, heart beats in the digitized acoustic heart sound signal that were detected with the highest level of confidence based on the predicted durations of the systole and diastole segments of the digitized acoustic heart sound signal and the peak array;
    g) determining, by the computing device, if segmentation of the digitized acoustic heart sound signal is possible based on the selected and isolated heart beats;
    h) if segmentation of the heart sound signal is found to be possible, dividing, by the computing device, inter-peak intervals that make up the digitized acoustic heart sound signal into even and odd groups in the order in which they appear;
    i) calculating, by the computing device, a variance and mean for both of the even and odd groups and designating the group with the largest ratio of variance over mean as corresponding to diastole intervals and the other group as corresponding to systole intervals; and
    j) outputting, by the computing device, the digitized acoustic heart sound signal with the selected and isolated heart beats and the designated diastole and systole intervals.

2. A process as claimed in claim 1, wherein predicting the durations of the systole and diastole segments of the digitized acoustic heart sound signal further includes:
    calculating, by the computing device, an envelope signal from the digitized acoustic heart sound signal;
    applying, by the computing device, a peak-peeling algorithm to the envelope signal of the digitized acoustic heart sound signal to create a peaks signal;
    finding, by the computing device, peak locations within the digitized acoustic heart sound signal by means of a peak finding algorithm which utilised the peaks signal;
    predicting, by the computing device, an average resting heart rate for the patient based on a received age of the patient;
    determining, by the computing device, whether the peak finding algorithm has found peak locations corresponding to both S1 and S2 heart sounds in the digitized acoustic heart sound signal or only one of them by calculating heart rates representative of both scenarios based on the distances between the peak locations in the peak array, and comparing the calculated heart rates to the average resting heart rate; and
    if it is determined that both the S1 and S2 heart sounds were found by the peak finding algorithm, predicting, by the computing device, the duration of the systole and diastole segments of the heart sound signal by using Burke's formula for male or female patients.

3. A process as claimed in claim 2, wherein calculating the envelope signal from the digitized acoustic heart sound signal further includes splitting, by the computing device, the digitized acoustic heart sound signal into short segments and calculating, by the computing device, a principal component for each segment, the principal components of each segment forming the envelope signal.

4. A process as claimed in claim 2, further including determining, by the computing device, a second prediction of the durations of the systole and diastole segments of the digitized acoustic heart sound signal by calculating an autocorrelation of the peaks signal to obtain an autocorrelation signal, locating, by the computing device, a central peak and three other peaks closest to the central peak in the autocorrelation signal and determining, by the computing device, the average systole and diastole durations based on the intervals between these peaks.

5. A process as claimed in claim 1, further including refining the peak locations in the peak array by:
    setting, by the computing device, a minimum and a maximum threshold for the systole duration;
    marking, by the computing device, intervals between peak locations that fall within the minimum and maximum thresholds as possible systolic intervals;
    identifying, by the computing device, an interval that is shorter than the minimum threshold as an irregular interval, the irregular interval being positioned between a first and second peak location in the peak array;
    removing, by the computing device, the second peak location from the peak array if an interval immediately before the irregular interval has been marked as a systolic interval, or removing, by the computing device, a smaller of the first and second peak locations from the peak array if neither the interval immediately before the irregular interval, nor an interval immediately thereafter has been marked as a systolic interval; and
    repeating the steps until no peaks were added or removed during a last iteration.

6. A process as claimed in claim 5, wherein setting the minimum and maximum threshold for the systole duration includes setting the minimum duration at 80% of an average systole length and setting the maximum duration at 120% of the average systole length.

7. A process as claimed in claim 5, wherein refining the peak locations in the peak array includes recovering, by the computing device, potentially lost peaks, which in turn includes:
    setting, by the computing device, a maximum threshold for a diastole duration;
    identifying, by the computing device, an interval that is longer than the maximum threshold as an irregular interval corresponding to a potentially missing peak, the irregular interval being positioned between a first and second peak location in the peak array;

assuming, by the computing device, the missing peak to be in the irregular interval;

searching, by the computing device, for the missing peak by looking for a maximum value in a corresponding region in the envelope signal;

adding, by the computing device, a peak to the peak array at a position corresponding to the maximum value if the maximum value is higher than a fixed threshold, alternatively, looking for a second maximum value in a Shannon energy envelope of the digitized acoustic heart sound signal and adding a peak to the peak array if the second maximum value is above a threshold, alternatively, adding no additional peak in the peak array; and repeating the steps until no changes were made to the peaks array during a last iteration.

8. A process as claimed in claim 7, wherein setting the maximum threshold for the diastole durations includes setting the maximum threshold at 120% of an average diastole length.

9. A process as claimed in claim 1, wherein selecting and isolating the most confidently detected heart beats further includes:

calculating, by the computing device, a nominal heart rate for the patient by determining the autocorrelation of the digitized acoustic heart sound signal;

calculating, by the computing device, an instantaneous heart rate for every heart beat represented by two adjacent peak intervals in the peak array;

comparing, by the computing device, the instantaneous heart rate for every heart beat to the nominal heart rate; and disregarding, by the computing device, heart beats of which the instantaneous heart rate differs from the nominal heart rate by more than a predefined percentage and regarding the others.

10. A process as claimed in claim 9, wherein the predefined percentage is 15%.

11. A process as claimed in claim 9, wherein determining if segmentation of the digitized acoustic heart sound signal is possible includes determining if more than a predefined number of consecutive heart beats have been regarded.

12. A process as claimed in claim 1, wherein outputting the digitized acoustic heart sound signal with the selected and isolated heart beats and the designated diastole and systole intervals includes outputting to a diagnostic decision network that determines whether or not the patient's heart has a pathological murmur.

* * * * *